US005733873A

United States Patent [19]
Österberg et al.

[11] Patent Number: 5,733,873
[45] Date of Patent: Mar. 31, 1998

[54] COMPOSITION COMPRISING COAGULATION FACTOR VIII FORMULATION, PROCESS FOR ITS PREPARATION AND USE OF A SURFACTANT AS STABILIZER

[75] Inventors: Thomas Österberg; Angelica Fatouros, both of Stockholm, Sweden

[73] Assignee: Pharmacia & Upjohn AB, Stockholm, Sweden

[21] Appl. No.: 244,266

[22] PCT Filed: Oct. 1, 1993

[86] PCT No.: PCT/SE93/00793

§ 371 Date: May 20, 1994

§ 102(e) Date: May 20, 1994

[87] PCT Pub. No.: WO94/07510

PCT Pub. Date: Apr. 14, 1994

[30] Foreign Application Priority Data

| Oct. 2, 1992 | [SE] | Sweden | 9202878 |
| May 7, 1993 | [SE] | Sweden | 9301580 |
| Jun. 11, 1993 | [SE] | Sweden | 9302006 |

[51] Int. Cl.$^6$ .......................... A61K 38/37; A61K 38/36; C07K 14/745; C07K 14/755
[52] U.S. Cl. .......................... 514/12; 514/21; 514/834; 530/383; 530/417; 530/830
[58] Field of Search .......................... 530/383, 829, 530/830, 412–417; 514/12, 21, 834

[56] References Cited

U.S. PATENT DOCUMENTS

| 4,165,370 | 8/1979 | Coval | 424/177.1 |
| 4,597,966 | 7/1986 | Zolton et al. | 424/141.1 |
| 4,783,441 | 11/1988 | Thurow | 514/3 |
| 4,877,608 | 10/1989 | Lee et al. | 424/176.1 |
| 5,118,794 | 6/1992 | Grangeorge et al. | 530/363 |
| 5,328,694 | 7/1994 | Schwinn | 424/423 |

FOREIGN PATENT DOCUMENTS

| A-14702/92 | 10/1992 | Australia . |
| 0 099 445 A2 | 2/1984 | European Pat. Off. . |
| 0 268 110 A1 | 5/1988 | European Pat. Off. . |
| 0 367 746 A2/A3 | 5/1990 | European Pat. Off. . |
| WO 89/09614 | 10/1989 | WIPO . |
| 9109122 | 6/1991 | WIPO . |
| WO 91/10439 | 9/1991 | WIPO . |

*Primary Examiner*—Nancy Degen
*Attorney, Agent, or Firm*—Pollock, Vande Sande & Priddy

[57] ABSTRACT

A composition comprising coagulation factor VIII and a non-ionic surfactant such as block copolymers, e.g., poly-oxamers or polyoxyethylene (20) sorbitan fatty acid esters, e.g., polysorbate 20 or polysorbate 80 as stabilizer is provided. The composition can also comprise sodium chloride, calcium chloride, L-histidine and/or sugars or sugar alcohols.

35 Claims, 1 Drawing Sheet

COMPOSITION COMPRISING COAGULATION FACTOR VIII FORMULATION, PROCESS FOR ITS PREPARATION AND USE OF A SURFACTANT AS STABILIZER

The present invention relates to a novel formulation comprising coagulation factor VIII and a non-ionic surfactant such as block co-polymers, e.g. polyoxamers or polyoxyethylene (20) sorbitan fatty acid esters e.g. polysorbate 20 or polysorbate 80. The composition can also comprise sodium chloride, calcium chloride, L-histidine and/or sugars and/or sugar alcohols.

Haemophilia is an inherited disease which has been known for centuries but it is only within the last three decades that it has been possible to differentiate between the various forms; haemophilia A, haemophilia B and haemophilia C. Haemophilia A is the most frequent form. It affects only males with an incidence of one or two individuals per 10,000 live-born males. The disease is caused by strongly decreased level or absence of biologically active coagulation factor VIII (antihaemophilic factor) which is a protein normally present in plasma. The clinical manifestation of haemophilia A is a strong bleeding tendency and before treatment with factor VIII concentrates was introduced, the mean age of those patients was less than 20 years. Concentrates of factor VIII obtained from plasma have been available for about three decades. This has improved the situation for treatment of haemophilia patients considerably and given them possibility to live a normal life.

Therapeutic factor VIII concentrates have until now been prepared by fractionation of plasma. However, there are now methods available for production of factor VIII in cell culture using recombinant DNA techniques as reported in e.g. J Gitschier et al. Nature 312, 330–37, 1984 and EP 160 457.

Factor VIII concentrates derived from human plasma contain several fragmented fully active factor VIII forms (Andersson et al, Proc. Natl. Acad. Sci. USA, Vol 83,2979–83, May 1986). The smallest active form has a molecular mass of 170 kDa and consists of two chains of 90 kDa and 80 kDa held together by a metal ion bridge. Reference is here made to EP 197 901. Kabi Pharmacia has developed a recombinant factor VIII product which corresponds to the 170 kDa plasma factor VIII form in therapeutic factor VIII concentrates. The truncated recombinant factor VIII molecule is termed r-VIII SQ and is produced by Chinese Hamster Ovary (CHO) cells in a cell culture process in serum free medium at finite passage.

The specific activity of r-VIII SQ could be more than 12,000 IU/mg protein and preferably more than 14,000 IU/mg. Activity of about 15,000 IU/mg has been measured. About 10,000 IU VIII:C per mg protein has earlier been known for our r-VIII SQ.

Recombinant factor VIII SQ is indicated for treatment of classical haemophilia. The dosage is similar to the dosage of the plasma factor VIII concentrates. Due to the high concentration now obtainable only small volumes are needed for injection.

The structure and biochemistry of recombinant factor VIII-products in general have been described by Kaufman Tibtech, Vol 9,1991 and Hematology, 63, 155–65, 1991. The structure and biochemistry of r-VIII SQ have been described in WO 91/09122.

The stability of proteins is generally a problem in pharmaceutical industry. It has often been solved by drying of the protein in different drying processes, such as freeze drying. The protein has thereafter been distributed and stored in dried form. The solution before drying or freeze-drying, the dried material and the reconstituted product should all be stable, so that not too much activity is lost during the drying process, the storage or during handling.

Factor VIII which has been fractionated from plasma is normally sold as lyophilized powder which should be reconstituted with water.

A formulation with a low amount of protein will generally loose activity during purification, sterile manufacturing, in the package and during the administration. This problem is usually solved by the addition of human albumin which reduces the activity loss of the active protein considerably. Human albumin functions as a general stabilizer during purification, sterile manufacturing and freeze-drying (see review by Wang et al., J. of Parenteral Sci. and Tech. Vol 42, Number 2S, supplement. 1988). Human albumin is also a good cake-former in a formulation for freeze-drying. The use of albumin for stabilization of factor VIII is known and is currently used in all highly purified factor VIII products on the market. However, it is not desirable to add human albumin to a therapeutic protein manufactured by recombinant DNA technology. In addition, the use of human albumin as a formulation excipient often limits the use of many of the most powerful and sensitive analytical methods for protein characterization.

There is a need for albumin free formulations containing factor VIII and especially recombinant factor VIII which are stable during drying or freeze-drying, in solution and as a solution after reconstitution.

Several solutions have been proposed for the stabilization of different proteins:

EP 35 204 (Cutter) discloses a method for imparting thermal stability to a protein composition in the presence of a polyol.

EP 381 345 (Corint) discloses an aqeous liquid of a peptide, desmopressin, in the presence of carboxymethylcellulose.

In WO 89/09614 (Genentech), a stabilized formulation of human growth hormone comprising glycine, mannitol and a buffer is disclosed and in a preferred embodiment a non-ionic surfactant such as polysorbate 80 is added. The non-ionic surfactant is added for reduced aggregation and denaturation. The formulation has an increased stability in a lyophilized formulation and upon reconstitution.

EP 268 110 (Cetus) discloses a solution comprising a particular protein, interleukin-2, which is dissolved in an inert carrier medium comprising a non-ionic polymeric detergent as a solubilizer/stabilizer. The preferred detergents are octylphenoxy polyethoxy ethanol compounds, polyethylene glycol monostearate compounds and polyethylene sorbitan fatty acid esters.

U.S. Pat. No. 4,783,441 (Hoechst)discloses an aqueous solution comprising a protein, such as insulin and a surface active substance.

U.S. Pat. No. 4,165,370 (Coval) discloses a gamma globulin solution and a process for the preparation thereof. The solutions contains polyethylene glycol (PEG). A non-ionic surfactant can be added to the solution.

In EP 77 870 (Green Cross) the addition of amino acids, monosaccarides, oligosaccarides or sugar alcohols or hydrocarbon carboxylic acid to improve stability of a solution containing factor VIII is disclosed and the addition of sugar alcohol or disaccarides to an aqueous solution of factor VIII for increasing stability during heat treatment has been disclosed in EP 117 064 (Green Cross).

WO 91/10439 (Octopharma) claims stable injectable solution of factor VIII or factor IX which comprises a disaccaride, preferably saccarose and one or more amino acids.

EP 315 968 and EP 314 095 (Rorer) claim stable formulations of factor VIII with different ionic strength.

Proteins are different with regard to physico-chemical properties. When preparing a pharmaceutical preparation which should be physico-chemical acceptable, and stable for a long time, consideration can not only be taken to the physiological properties of the protein but also other aspects must be considered such as the industrial manufacture, easy handling for the patient and safety for the patient. The results of these aspects are not predictable when testing different formulations and there often is a unique solution for each protein.

In plasma circulating factor VIII is stabilized by association with its carrier protein, the von Willebrand factor (vWF). In plasma and also in conventional intermediate purity factor VIII concentrates the ratio vWF to factor VIII is at least 50:1 on a weight basis. In very high purity factor VIII concentrates, with a specific activity of more than 2 000 IU per mg protein, the ratio vWF to factor VIII is about 1:1 (w/w) and essentially all factor VIII is bound to vWF. Despite this stabilization further protection by the addition of albumin is required in order to achieve an acceptable stability during lyophilization and storage.

All super pure preparations on the market are stabilized with albumin (human serum albumin). There is a now a demand for injectable factor VIII without albumin and containing a minimum of additives.

We have now developed a new formulation which solves the above mentioned problems for factor VIII.

To our great surprise we have found that factor VIII, which is a very sensitive protein, can be stabilized without albumin, when a non-ionic surfactant is added.

Thus the present invention relates to a composition comprising a coagulation factor VIII and a non-ionic surfactant as stabilizer. Our factor VIII is highly purified, i.e. has a specific activity of more than 5000 IU/mg protein, and the composition is stabilized without the addition of albumin. When factor VIII is recombinant it can be either in its full-length form or as a deletion derivative such as SQ derivative. The amount of factor VIII is from 10 to 100,000 IU/ml, preferably 50 to 10,000 IU/ml. The non-ionic surfactant is preferably chosen from block co-polymers such as a poloxamer or polyoxyethylene (20) fatty acid ester, such as polysorbate 20 or polysorbate 80. Tween 80® has been used as polysorbate 80. The non-ionic surfactant should be present in an amount above the critical micelle concentration (CMC). See Wan and Lee, Journal of Pharm Sci, 63, 136, 1974. The polyoxyethylene (20) fatty acid ester is thus preferably in an amount of at least 0.01 mg/ml. The amount could e.g. be between 0.02 and 1 mg/ml. The composition can also comprise sodium or potassium chloride, preferably in an amount of more than 0.1M.

The composition comprises preferably a calcium salt such as calcium chloride or calcium gluconate preferably in an amount of more than 0.5 mM and an amino acid such as L-histidine in an amount of more than 1 mM. The amount could e.g. be chosen between 0.05 and 500 mM. Mono-or disaccarides such as sucrose or sugar alcohols could be added e.g. in an amount of 1 to 300 mg/ml.

The composition comprises preferably L-histidine and sucrose. The ratio sodium chloride to L-histidine in the composition is preferably more than 1:1.

The composition could comprise i) 10–100,000 IU/ml of recombinant factor VIII ii) at least 0.01 mg/ml. of a polyoxyethylene (20) fatty acid ester iii) sodium chloride, preferably in an amount of more than 0.1M.

iv) calcium salt such as calcium chloride or calcium gluconate preferably in an amount of more than 0.5 mM.

v) an amino acid such as L-histidine in an amount of more than 1 mM.

To this composition could mono-or disaccarides or sugar alcohols, preferably sucrose be added. The composition could be in a dried form, preferably lyophilized or in aqeous solution before or after drying. The dried product is reconstituted with sterile water for injection or a buffer solution.

The claimed composition can also be a stable aqeous solution ready for use.

The invention also relates ot compositions in which the specific activity of r-VIII SQ is more than 12,000 IU/mg protein, preferably more than 14,000 IU/mg.

The claimed composition can be prepared by mixing factor VIII with a non-ionic surfactant in an aqeous solution, preferably together with an amino acid such as L-histidine, sodium salt, sucrose and a calcium salt or by eluating factor VIII from the last purification step with a buffer containing a non-ionic surfactant in an aqeous solution, preferably together with an amino acid such as L-histidine, sodium salt, sucrose and a calcium salt.

The invention also relates to the use of a non ionic surfactant preferably chosen from block co-polymers, preferably a poloxamer or polyoxyethylene (20) fatty acid ester, preferably polysorbate 20 or polysorbate 80, as stabilizer for a composition comprising coagulation factor VIII.

An amino acid is used to buffer the system and it protects also the protein in the amorphous phase. A suitable buffer could be L-histidine, lysine and/or arginine. L-Histidine has primarily been chosen because of the good buffer capacity of L-histidine around pH 7.

Sucrose or sugar alcohol can also be added for the protection of the protein.

Calcium (or divalent metal ions), here added as calcium chloride ($CaCl_2$) but other salts such as calcium gluconate, calcium glubionate or calcium gluceptate can also be used, is necessary for the maintenance of the association of factor VIII heavy and light chain.

The data presented in the examples indicate that r-VIII SQ is stable for at least 12 months when stored at $5°\pm3°$ C.

The following examples illustrate the invention and show stability data for different formulations, all falling under the patent protection, a protection which is not limited to these examples.

EXPERIMENTAL

Material and Methods

Figure 1:
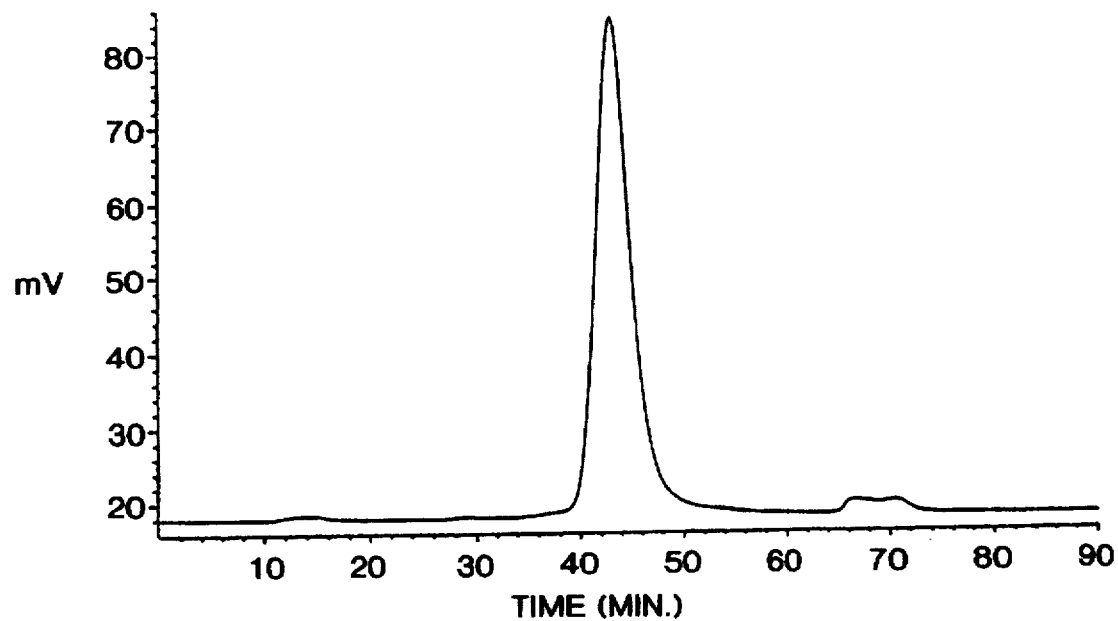
FIG. 1 HPLC gelfiltration, Example 10A, stored 5 months at 25° C.

The production of recombinant factor VIII SQ (r-VIII SQ) was essentially performed as described in patent WO 91/09122, example 1–3. A DHFR deficient CHO celline (DG44N.Y.) was electroporated with an expression vector containing the r-VIII SQ gene and an expression vector containing the dihydrofolate-reductase gene. Following selection on selective media surviving colonies were amplified through growth in stepwise increasing amounts of methotrexate. Supernatant from the resulting colonies were individually screened for VIII:C activity. A production done was chosen and this was subsequently adapted to serum free suspension growth in a defined medium and finally a large scale fermentation process was developed. Supernantant is collected after certain time periods and further purified as described below.

The clarified conditioned medium was pH adjusted and applied to a S-Sepharose FF column. After washing, factor VIII was eluated with a salt buffer containing 5 mM $CaCl_2$.

Immunoadsorption was carried out on an immunoaffinity resin where the ligand was a monoclonal antibody (8A4) directed towards the heavy chain of Factor VIII. Before loading to the column the S-eluate was treated with 0.3% TNBP and 1% Octoxynol 9. The column was equilibrated, washed and factor VIII was eluated with a buffer containing 0.05M $CaCl_2$ and 50% ethylene glycol.

The mAb-eluate was loaded on a Q-Sepharose FF column, equilibrated with the elution buffer in the immunoaffinity step. After washing, factor VIII was eluated with 0.05M L-histidine, 4 mM $CaCl_2$, 0.6M NaCl, pH 6.8.

The Q-eluate was applied to a gel filtration column (Superdex 200 p.g.). Equilibration and elution was carried out with a formulation containing sodium chloride, L-histidine, calcium chloride and polysorbate 80.

The protein peak was collected and the solution was formulated before freeze drying.

The VIII:C activity and the concentration of the inactive components were adjusted by diluting with an appropriate buffer. The solution was then sterile filtered (0.22 µm), dispensed and freeze-dried. Samples from each composition were frozen and stored at $-70\,°$ C. These samples were thawed and used as references during the assay of VIII:C.

The coagulant activity VIII:C was assessed by a chromogenic substrate assay (Coatest Factor VIII, Chromogenix AB, Mölndal, Sweden). Activated factor X (Xa) is generated via the intrinsic pathway where factor VIII:C acts as cofactor. Factor Xa is then determined by the use of a synthetic chromogenic substrate, S-2222 in the presence of a thrombin inhibitor I-2581 to prevent hydrolysis of the substrate by thrombin. The reaction is stopped with acid, and the VIII:C, which is proportional to the release of pNA (paranitroaniline), is determined photometrically at 450 nm against a reagent blank. The unit of factor VIII:C is expressed in international units (IU) as defined by the current International Concentrate Standard (IS) established by WHO.

The recovery of VIII:C is calculated as the percentage of VIII:C in the reconstituted solution divided by the VIII:C in the frozen and thawed solution for freeze-drying with appropriate adjustment for dilutions.

Soluble aggregates were determined by gel filtration. A prepacked Superdex 200 HR 10/30 column (Pharmacia) was used with a fluoroscence detector (exitation wavelength 280 nm), emission wavelength 340 nm). The reconstituted preparation were analysed. Evaluation of results from gel-filtration was done by visual examination of the chromatograms, or by integration of the peak areas if aggregates were found.

Recovery over freeze drying is expressed in % yield of frozen reference.

EXAMPLE 1

Comparison Between Albumin and Non-ionic Surfactant

Recombinant factor VIII was prepared according to the method described under Experimental.

Two ml of the solution was lyophilized and thereafter reconstituted in an amount of 5 ml of sterile water for injections.

The compositions were the following:

|  | 1A | 1B | 1C | 1D |
|---|---|---|---|---|
| L-Histidine, mM | 50 | 50 | 50 | 50 |
| Sodium chloride, M | 0.6 | 0.6 | 0.6 | 0.6 |
| Calcium chloride, mM | 4 | 4 | 4 | 4 |
| Polysorbate, 80, % | — | — | 0.02 | — |
| PEG 4000, % | 0.1 | 0.1 | — | — |
| Albumin, % | — | 1 | — | 1 |
| VIII:C charged IU/ml | 250 | 250 | 250 | 250 |
| Recovery, IU/ml after reconsist. | 83 | 197 | 232 | 222 |

This example shows that there was no difference in the recovery of factor VIII:C when the non ionic surfactant or albumin was used.

EXAMPLE 2

Comparison Between Different Strengths of Non Ionic Surfactant

Recombinant factor VIII was prepared according to the method described under Experimental.

Two ml of the solution was lyophilized and thereafter reconstituted in an amount of 2 ml of sterile water for injections.

The compositions were the following:

|  | 2A | 2B | 2C |
|---|---|---|---|
| L-Histidine/L-Glutamate equimolar amount, mg/ml | 10 | 10 | 10 |
| Sodium chloride, % | 2 | 2 | 2 |
| Calcium chloride, mg/ml | 0.1 | 0.1 | 0.1 |
| Polysorbate 80, % | — | 0.001 | 0.01 |
| VIII:C charged IU/ml | 300 | 300 | 300 |
| Recovery, IU/ml after reconstit. |  |  |  |
| Initial | 69 | 133 | 228 |
| 3.5 h* | 43 | 140 | 222 |
| 7 h* | 49 | 133 | 204 |

*stored as reconstituted solution at ambient temperature

It is here clearly shown the surprisingly good stabilizing effect on factor VIII when a non ionic surfactant is used.

EXAMPLE 3

Variation of Non-ionic Surfactant Concentration

Recombinant factor VIII was prepared according to the method described under Experimental.

Two ml of the solution was lyophilized and thereafter reconstituted in an amount of 5 ml of sterile water for injections.

|  | 3A | 3B | 3C | 3D | 3E |
|---|---|---|---|---|---|
| L-Histidine, mM | 50 | 50 | 50 | 50 | 50 |
| Sodium chloride, M | 0.34 | 0.34 | 0.34 | 0.34 | 0.34 |
| Calcium chloride, mM | 4 | 4 | 4 | 4 | 4 |

-continued

|  | 3A | 3B | 3C | 3D | 3E |
|---|---|---|---|---|---|
| Polysorbate 80, % | 0.01 | 0.02 | 0.03 | 0.04 | 0.05 |
| Recovery, after reconstit., % | 91 | 90 | 93 | 99 | 100 |

Results from this example indicate that the recovery of factor VIII (VIII:C) was very high after reconstitution and good for all concentrations of polysorbate 80 used.

EXAMPLE 4

Variation of Sodium Chloride Concentration

Recombinant factor VIII was prepared according to the method described under Experimental.

Two ml of the solution was lyophilized, stored at different temperatures for up to 6 months (mon) and thereafter reconstituted in an amount of 5 ml of sterile water for injections.

|  | 4A | 4B |
|---|---|---|
| L-Histidine, mM | 50 | 50 |
| Sodium chloride, M | 0.3 | 0.6 |
| Calcium chloride, mM | 4 | 4 |
| PEG-4000% (Polyethylene glycol) | 0.1 | 0.1 |
| Polysorbate 80, % | 0.025 | 0.025 |
| Recovery, %, initial stored at 8° C. | 85 | 86 |
| 3 mon | 88 | 87 |
| 4 mon | 87 | 83 |
| 6 mon | 87 | 83 |
| stored at 25° C., |  |  |
| 1 mon | 92 | 93 |
| 3 mon | 87 | 79 |
| 4 mon | 84 | 81 |
| 6 mon | 85 | 85 |
| stored at 37° C. |  |  |
| 1 mon | 88 | 90 |
| 3 mon | 80 | 80 |
| 4 mon | 80 | 77 |
| 6 mon | 81 | 80 |
| stored at 50° C. |  |  |
| 1 mon | 84 | 89 |
| 3 mon | 77 | 77 |
| 4 mon | 73 | 70 |

0.3 or 0.6M sodium chloride showed very good stability. Both formulations were stable for 6 months at 37° C.

EXAMPLE 5

Variation of L-Histidine Concentration

Recombinant factor VIII was prepared according to the method described under Experimental.

2.2 ml of the solution was lyophilized, stored at different temperatures for up to 3 months (mon) and thereafter reconstituted in an amount of 5 ml of sterile water for injections.

|  | 5A | 5B |
|---|---|---|
| L-Histidine, mM | 46 | 59 |
| Sodium chloride, M | 0.31 | 0.31 |
| Calcium chloride, mM | 3.7 | 3.7 |
| PEG-4000% (Polyethylene glycol) | 0.091 | 0.091 |
| Polysorbate 80, % | 0.364 | 0.364 |
| Recovery, % |  |  |
| stored at 8° C., |  |  |
| Initial | 78 | 84 |
| 3 mon | 70 | 76 |
| stored at 25° C., | 1 mon |  |
| 1 mon |  |  |
| 3 mon | 69 | 74 |
| stored at. 37° C. |  |  |
| 1 mon | 76 | 85 |
| 3 mon | 61 | 48 |
| stored at 50° C. |  |  |
| 1 mon | 60 | 73 |
| 3 mon | 44 | 48 |

This example shows that these different amounts of L-histidine does not effect the stability.

EXAMPLE 6

Recombinant factor VIII was prepared according to the method described under Experimental.

|  | 6A | 6B |
|---|---|---|
| L-Histidine, mM | 65 | 65 |
| Sodium chloride. M | 0.3 | 0.3 |
| Calcium chloride, mM | 4 | 4 |
| PEG-4000% | 0 | 0.1 |
| Tween 80, % | 0.025 | 0.025 |

These solutions were freezed/thawed 1, 5 and 10 times and the recovery was the following:

|  | IU/ml | IU/ml |
|---|---|---|
| cold | 298 | 291 |
| 1 freezing | 293 | 293 |
| 5 | 295 | 287 |
| 10 | 290 | 288 |

These studies showed that VIII:C was stable after repeated freeze-thawing and that PEG-4000, which is thought to act as cryoprotectant, is not necessary in this formulation.

EXAMPLE 7

Variation of pH

Recombinant factor VIII was prepared according to the method described under Experimental.

2.2 ml of the solution was lyophilized and thereafter reconstituted in an amount of 5 ml of sterile water for injections.

|                    | 7A    | 7B    | 7C    | 7D    |
|--------------------|-------|-------|-------|-------|
| L-Histidine, mM    | 65    | 65    | 65    | 65    |
| Sodium chloride, M | 0.3   | 0.3   | 0.3   | 0.3   |
| Calcium chloride, mM | 4   | 4     | 4     | 4     |
| Polysorbate 80, %  | 0.025 | 0.025 | 0.025 | 0.025 |
| pH                 | 6.0   | 6.5   | 7.0   | 7.5   |
| Recovery, %, Initial | 74  | 70    | 78    | 79    |
| 3 hours*           | 73    | 80    | 78    | 77    |

*stored as reconstituted solution at ambient temperature

EXAMPLE 8

Addition of Sucrose

Recombinant factor VIII was prepared according to the method described under Experimental.

2.2 ml of the solution was lyophilized and thereafter reconstituted in an amount of 5 ml of sterile water for injections.

|                      | 8A    | 8B     |
|----------------------|-------|--------|
| L-Histidine, mM      | 58    | 20.5   |
| Sodium chloride. M   | 0.3   | 0.3    |
| Calcium chloride, mM | 3.7   | 3.7    |
| Sucrose, mM          | 0     | 13.3   |
| Polysorbate 80, %    | 0.025 | 0.0.25 |

Sucrose was added to the solution B after the final purification step before lyophilization.

The recovery after freeze-drying was 76% for A and 87% for B. The same activity was found 4 hours after reconstitution stored at room temperature.

This study indicated that the addition of sucrose is favourable for the recovery of VIII:C over freeze-drying.

EXAMPLE 9

Variation of Calcium Salt

Recombinant factor VIII was prepared according to the method described under Experimental.

Two ml of the solution was lyophilized and thereafter reconstituted in an amount of 5 ml of sterile water for injections.

|                      | 9A    | 9B    | 9C    | 9D    |
|----------------------|-------|-------|-------|-------|
| L-Histidine, mM      | 23    | 23    | 23    | 23    |
| Sodium chloride, M   | 0.34  | 0.34  | 0.34  | 0.34  |
| Calcium chloride, mM | 4     | 4     | 0.15  | 0.15  |
| Polysorbate, %       | 0.025 | 0.025 | 0.025 | 0.025 |
| Sucrose, mM          | —     | 10    | —     | 10    |
| Calciumgluconate, mM | 0     | 0     | 6     | 6     |
| Recovery, %, Initial | 63    | 74    | 74    | 78    |
| 4 hours*             | 60    | 73    | 73    | 77    |

*stored as reconstituted solution at ambient temperature

This example shows that $CaCl_2$ can be substituted by Calcium gluconate.

EXAMPLE 10

Recombinant factor VIII was prepared according to the method described under Experimental.

2.2 ml of the solution was lyophilized and thereafter reconstituted in an amount of 5 ml of sterile water for injections. VIII:C per vial in reconstituted preparation was about 1000 IU.

|                                         | 10A   | 10B   |
|-----------------------------------------|-------|-------|
| L-Histidine, mM                         | 14.7  | 58    |
| Sodium chloride. M                      | 0.31  | 0.31  |
| Calcium chloride, mM                    | 3.7   | 3.7   |
| Sucrose, mM                             | 19.9  | —     |
| Polysorbate 80, %                       | 0.025 | 0.025 |
| Recovery, IU/ml after reconstitution    |       |       |
| Initial                                 | 213   | 198   |
| 4 h, 25° C.                             | 213   | 198   |
| 24, 25° C.                              | 201   | 182   |
| Recovery, %                             |       |       |
| Initial                                 | 92    | 91    |
| 5 months, 25° C.                        | 88    | —     |
| 5 months, 30° C.                        | 76    | 85    |
| 12 months, 7° C.                        | 89    | 97    |

The recovery was good when part of the L-histidine was substituted by sucrose.

Figure 2:
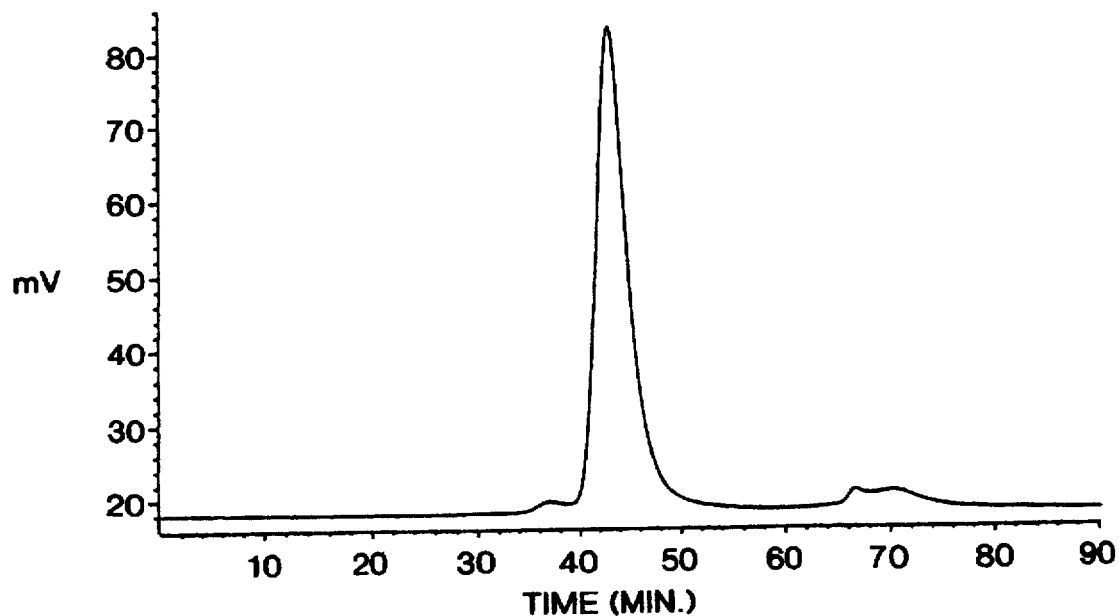
FIG. 2 HPLC gelfiltration, Example 10B, stored 5 months at 30° C.

These formulations were studied by gelfiltration after 5 months storage at 25° C. and 30° C., respectively and the results are shown in FIGS. 1 and 2. The only peaks to be seen is the peak at 42, indicating factor VIII:C and the peak at 70 which is histidine. Aggregates is to be found earlier than 40. From FIG. 1 it can be seen that no detectable amount of aggregates was found after 5 months at 25° C. for 10A. FIG. 2 shows a small amount of aggregates which is less than 2% after 5 months at 30° C. for 10B.

EXAMPLE 11

Recombinant factor VIII was prepared according to the method described under Experimental.

2.2 ml of the solution was lyophilized and thereafter reconstituted in an amount of 5 ml of sterile water for injections. VIII:C per vial in reconstituted preparation was about 500 IU.

|                                      | 11A   | 11B   |
|--------------------------------------|-------|-------|
| L-Histidine, mM                      | 14.7  | 58    |
| Sodium chloride, M                   | 0.31  | 0.31  |
| Calcium chloride, mM                 | 3.7   | 3.7   |
| Sucrose, mM                          | 19.9  | —     |
| Polysorbate 80, %                    | 0.025 | 0.025 |
| Recovery, IU/ml after reconstitution |       |       |
| Initial                              | 98    | 105   |
| 4 h, 25° C.                          | 96    | 103   |
| 24, 25° C.                           | 93    | 101   |
| Recovery, %                          |       |       |
| Initial                              | 91    | 93    |
| stored at 25° C., 5 mon              | 89    | 87    |
| stored at 30° C., 5 mon              | 76    | 79    |
| stored at 7° C. 12 mon               | 88    | 89    |

Both formulations showed good stability. These formulations were studied by gelfiltration and the results were similar as shown in FIGS. 1 and 2. No aggregation was formed when the formulations had been stored for 5 months at 25° C. and 30° C., respectively.

EXAMPLE 12

Recombinant factor VIII was prepared according to the method described under Experimental.

2 ml of the solution was lyophilized, stored at different temperatures for up to 3 months (mon) and thereafter reconstituted in an amount of 4 ml of sterile water for injections. VIII:C per vial in reconstituted preparation was about 500 IU.

|  | 12A | 12B |
|---|---|---|
| Mannitol, mg/ml | 20 | 20 |
| L-Histidine, mg/ml | 2.67 | 2.67 |
| Sodium chloride, mg/ml | 18 | 18 |
| Calcium chloride, mM | 3.7 | 3.7 |
| Polysorbate 80, mg/ml | 0.23 | 0.23 |
| Recovery, % |  |  |
| initial | 91 | 93 |
| stored at. 7° C. 5 mon | 90 | 85 |

An acceptable stability was achieved after five months at 7° C.

We claim:

1. A composition comprising recombinant coagulation factor VIII with a specific activity of more than 5000 IU/mg protein and a non-ionic surfactant at a concentration between 0.01 mg/ml and 1 mg/ml for stabilizing the factor VIII's activity during storage for at least 6 months, wherein the composition is an aqueous solution ready for use or a composition dried and reconstituted before use and wherein said factor VIII is stable without the addition of albumin.

2. The composition according to claim 1 in which factor VIII is full-length or a deletion derivative of recombinant factor VIII.

3. The composition according to claim 2 wherein said factor VIII is a deletion derivative identified as r-VIII SQ and wherein the specific activity of said deletion derivative r-VIII SQ is more than 12,000 IU/mg protein.

4. The composition according to claim 3 wherein said specific activity is more than 14,000 IU/mg.

5. The composition according to claim 1 in which the concentration of factor VIII is 10 to 100,000 IU/ml.

6. The composition according to claim 1 in which the non-ionic surfactant is present at a concentration above critical micelle concentration.

7. The composition according to claim 1 in which the non-ionic surfactant is chosen from block co-polymers.

8. The composition according to claim 7 in which the polyoxyethylene (20) fatty acid ester is at a concentration of at least 0.01 mg/ml.

9. The composition according to claim 7 wherein said block co-polymers are poloxamer or polyoxyethylene (20) fatty acid ester.

10. The composition according to claim 7 wherein said block co-polymers are polysorbate 20 or polysorbate 80.

11. The composition according to claim 1 which comprises sodium or potassium chloride.

12. The composition according to claim 11 wherein said sodium or potassium chloride is present in a concentration of more than 0.1M.

13. The composition according to claim 11, which further comprises L-histidine and the ratio of said sodium or potassium chloride to L-histidine is more than 1:1.

14. The composition according to claim 1 which comprises a calcium salt.

15. The composition according to claim 14 wherein said calcium salt is calcium chloride or calcium gluconate and the concentration is more than 0.5 mM.

16. The composition according to claim 1, which comprises an amino acid at a concentration of more than 1 mM.

17. The composition according to claim 16 wherein said amino acid is L-histidine.

18. The composition according to claim 1, which comprises a saccharide selected from the group consisting of mono and disaccharides.

19. The composition according to claim 18 wherein said saccharide is sucrose or a sugar alcohol.

20. The composition according to claim 1 which comprises L-histidine and sucrose.

21. The composition according to claim 1, comprising
 i) 10–100,000 IU/ml of recombinant factor VIII,
 ii) at least 0.01 mg/ml of a polyoxyethylene (20) fatty acid ester,
 iii) sodium chloride,
 iv) a calcium salt
 v) an amino acid at a concentration of more than 1 mM.

22. The composition according to claim 21 wherein the concentration of said sodium chloride is more than 0.1M; the concentration of said calcium salt is more than 0.5 mM; said calcium salt is calcium chloride or calcium gluconate; and said amino acid is L-histidine.

23. The composition according to claim 1 which is dried.

24. The composition according to claim 23 which is lyophilized.

25. The composition according to claim 1 which is in a stable aqeous solution ready for use.

26. The composition according to claim 1, in which factor VIII is deletion derivative r-VIII SQ.

27. The composition according to claim 26, in which the composition is stable for at least 12 months at 2° to 8° C.

28. The composition according to claim 1 wherein the concentration of factor VIII is 50 to 10,000 IU/ml.

29. A method for treatment of hemophilia comprising administration of a therapeutically effective amount of the composition of claim 1.

30. A composition comprising:
 i) 10–100,000 IU/ml of recombinant factor VIII with a specific activity of more than 5000 IU/mg protein
 ii) between 0.01 and 1 mg/ml of a polyoxyethylene (20) fatty acid ester
 iii) sodium chloride at a concentration of more than 0.1M
 iv) calcium salt at a concentration of more than 0.5 mM
 v) an amino acid at a concentration of more than 1 mM;
 and wherein said factor VIII is stable without the addition of albumin.

31. A process for the preparation of a composition comprising recombinant coagulation factor VIII with a specific activity of more than 5000 IU/mg protein and a non-ionic surfactant at a concentration between 0.01 mg/ml and 1 mg/ml for stabilizing the factor VIII's activity during storage for at least 6 months, wherein said composition is an aqueous solution ready for use or a composition dried and reconstituted before use, comprising mixing said factor VIII with said non-ionic surfactant in an aqueous solution and wherein said factor VIII is stable without the addition of albumin.

32. The process of claim 31 which further comprises mixing with an amino acid, a sodium salt, sucrose and a calcium salt.

33. The process of claim 32 wherein said amino acid is L-histidine.

34. A process for the preparation of a composition comprising recombinant coagulation factor VIII with a specific activity of more than 5000 IU/mg protein and a non-ionic surfactant at a concentration between 0.01 mg/ml and 1 mg/ml for stabilizing the factor VIII's activity during storage for at least 6 months, wherein the composition is an aqueous solution ready for use or a composition dried and reconstituted before use, which comprises collecting supernatant from a fermentation broth for producing factor VIII and purifying said supernatant by subjecting it to a gel filtration column and then eluting factor VIII from the gel filtration column with a buffer containing a non-ionic surfactant in an aqueous solution and wherein said factor VIII is stable without the addition of albumin.

35. The process of claim 34 which further comprises eluting with an amino acid, a sodium salt, sucrose and a calcium salt.

* * * * *